US010245111B2

(12) United States Patent
Inoue et al.

(10) Patent No.: US 10,245,111 B2
(45) Date of Patent: Apr. 2, 2019

(54) OPERATION SUPPORT DEVICE

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 757 days.

(21) Appl. No.: 14/541,886

(22) Filed: Nov. 14, 2014

(65) Prior Publication Data

US 2015/0073436 A1    Mar. 12, 2015

Related U.S. Application Data

(63) Continuation of application No. PCT/JP2013/061747, filed on Apr. 22, 2013.

(30) Foreign Application Priority Data

May 18, 2012   (JP) .................................. 2012-114484

(51) Int. Cl.
    *A61B 34/00*       (2016.01)
    *A61B 34/20*       (2016.01)
    (Continued)

(52) U.S. Cl.
    CPC .............. *A61B 34/30* (2016.02); *A61B 34/70* (2016.02); *A61B 2034/2055* (2016.02);
    (Continued)

(58) Field of Classification Search
    None
    See application file for complete search history.

(56) References Cited

U.S. PATENT DOCUMENTS 6,425,865 B1 * 7/2002 Salcudean ............ A61B 8/0875
                                                   600/111
7,615,067 B2 * 11/2009 Lee ...................... A61B 17/062
                                                   604/528
(Continued)

FOREIGN PATENT DOCUMENTS

JP    2001-087281 A    4/2001
JP    2009-178416 A    8/2009
(Continued)

OTHER PUBLICATIONS

Extended Supplementary European Search Report dated Dec. 7, 2015 from related European Application No. 13 79 1225.9.
(Continued)

*Primary Examiner* — Michael J Carey
*Assistant Examiner* — Don N Ho
(74) *Attorney, Agent, or Firm* — Scully, Scott, Murphy & Presser, P.C.

(57) ABSTRACT

An operation support device includes a manipulation input unit and an operating section to which a surgical instrument is attached and which operates the surgical instrument. The surgical instrument includes a treatment section, a flexible insertion section, and a manipulation section which is fixed to the flexible insertion section. The manipulation input unit further includes a detection body which is attached to the manipulation section, and a detecting device which detects the detection body. The detecting device calculates information which is capable of specifying a position and/or an orientation of the detection body. On the basis of the information which is calculated by the detecting device, a control device controls an operation of the surgical instrument by outputting to the operating section an order of moving the surgical instrument as a manipulation order.

22 Claims, 14 Drawing Sheets

(51) Int. Cl.
*A61B 34/30* (2016.01)
*A61B 90/00* (2016.01)

(52) U.S. Cl.
CPC ... *A61B 2034/301* (2016.02); *A61B 2090/067* (2016.02); *A61B 2090/3983* (2016.02)

(56) References Cited

U.S. PATENT DOCUMENTS

| | | | |
|---|---|---|---|
| 2002/0133173 A1* | 9/2002 | Brock | A61B 34/20 606/130 |
| 2004/0111183 A1* | 6/2004 | Sutherland | A61B 34/70 700/245 |
| 2006/0258938 A1* | 11/2006 | Hoffman | A61B 1/00193 600/424 |
| 2006/0276686 A1* | 12/2006 | Tsuji | A61B 5/06 600/117 |
| 2007/0021738 A1* | 1/2007 | Hasser | A61B 8/4218 606/1 |
| 2007/0032906 A1* | 2/2007 | Sutherland | A61B 34/70 700/248 |
| 2007/0106147 A1* | 5/2007 | Altmann | A61B 8/12 600/407 |
| 2007/0156019 A1 | 7/2007 | Larkin et al. | |
| 2008/0287737 A1 | 11/2008 | Dejima | |
| 2009/0036902 A1* | 2/2009 | DiMaio | A61B 19/2203 606/130 |
| 2010/0256960 A1* | 10/2010 | Ortmaier | G06F 17/5018 703/7 |
| 2012/0221145 A1* | 8/2012 | Ogawa | B25J 3/04 700/259 |
| 2013/0303892 A1* | 11/2013 | Zhao | A61B 5/061 600/424 |
| 2014/0148820 A1* | 5/2014 | Ogawa | A61B 17/29 606/130 |

FOREIGN PATENT DOCUMENTS

| | | |
|---|---|---|
| JP | 2010-253162 A | 11/2010 |
| JP | 4672031 B | 4/2011 |
| JP | 2011-194163 A | 10/2011 |
| JP | 2011-237987 A | 11/2011 |
| WO | WO 2012/044334 A2 | 4/2012 |

OTHER PUBLICATIONS

Japanese Office Action dated Aug. 9, 2016 in related Japanese Patent Application No. 2012-114484.
International Search Report dated May 21, 2013 issued in PCT/JP2013/061747.
European Patent Office Communication dated Jun. 27, 2017 in corresponding European Application No. 13 791 225.9.

* cited by examiner

OPERATION SUPPORT DEVICE

FIELD OF THE INVENTION

The present invention relates to an operation support device manipulated through remote manipulation. This application is a continuation application based on PCT Patent Application No. PCT/JP2013/061747, filed Apr. 22, 2013, claiming priority based on Japanese Patent Application No. 2012-114484, filed May 18, 2012, the contents of which are incorporated herein by reference.

DESCRIPTION OF RELATED ART

In the related art, as a medical instrument used for surgery, an electric endoscope including a treatment tool channel into which a treatment tool is inserted is known (for example, see Japanese Patent No. 4672031).

In the medical instrument disclosed in Japanese Patent No. 4672031, a curving section of an electric endoscope is bent by using a joystick and various treatment tools are inserted into a treatment tool channel. Thus, the medical instrument disclosed in Japanese Patent No. 4672031 is configured to perform surgery.

SUMMARY OF THE INVENTION

An operation support device according to a first aspect of the present invention is an operation support device including a surgical instrument which includes a manipulation section provided at a proximal end side of the surgical instrument and operated by an operator, an insertion section provided at a distal end side of the manipulation section, and a treatment section provided at a distal end side of the insertion section; a slave manipulator which supports the surgical instrument and is configured to allow the treatment section to approach a treatment target; a manipulation section position-orientation detecting means which detects a position or an orientation of the manipulation section, and a control device which calculates a manipulation order based on information from the manipulation section position-orientation detecting means, and controls a position or an orientation of the surgical instrument by controlling a movement of the slave manipulator based on the manipulation order.

According to a second aspect, in the operation support device according to the first aspect, the manipulation section position-orientation detecting means may use a coordinate system with an origin which is set to have a predetermined positional relation with respect to the manipulation section.

According to a third aspect of the present invention, in the operation support device according to the first or second aspect, the manipulation section may include a marker, and the manipulation section position-orientation detecting means may detect a position or an orientation of the marker.

According to a fourth aspect of the present invention, in the operation support device according to any one of the first to third aspects, the manipulation section may include an indicator section configured to enable the manipulation section position-orientation detecting means to identify geometric characteristics of the manipulation section, and the manipulation section position-orientation detecting means may identify the indicator section, and sets the origin of the coordinate system.

According to a fifth aspect of the present invention, in the operation support device according to any one of the first to fourth aspects, the slave manipulator may include a hollow section, into which the insertion section is inserted, and which opens to a distal end section of the slave manipulator, and the treatment section may protrude from or withdraws into an opening formed in a distal end section of the hollow section According to a sixth aspect of the present invention, in the operation support device according to any one of the first to fifth aspects, the slave manipulator may include a treatment section moving mechanism configured to move the treatment section by holding the distal end side of the insertion section and bending the distal end side of the insertion section.

According to a seventh aspect of the present invention, in the operation support device according any one of the first to sixth aspects, the manipulation section may include a detected part provided for detecting the position or the orientation of the manipulation section by the manipulation section position-orientation detecting means, the detected part may be configured to be provided detachably at the manipulation section.

According to an eighth aspect of the present invention, in the operation support device according to any one of the first to seventh aspects, the detected part may further include an adapter attached to the manipulation section, and the manipulation section position-orientation detecting means may include an articulated arm connected to the adapter and the manipulation section position-orientation detecting means may detect the position or the orientation of the manipulation part by using a position or an orientation of the manipulation section.

According to a ninth aspect of the present invention, in the operation support device according to the seventh or eighth aspect, the detected part may be sterilizable.

According to a tenth aspect of the present invention, in the operation support device according to the seventh aspect, the detected part may be attached to the manipulation section via an intermediate member which is configured to be sterilized.

According to a eleventh aspect of the present invention, a surgical instrument used for an operation support device which comprises a manipulation section position-orientation detecting means, detects a position or an orientation of the surgical instrument, and a control device which calculates a manipulation order by an information from the manipulation section position-orientation detecting means, and controls the position or the orientation of the surgical instrument by controlling a movement of the slave manipulator based on the manipulation order, the surgical instrument comprising: a manipulation section provided at a proximal end side of the surgical instrument and operated by an operator; an insertion section provided at a distal end side of the manipulation section; a treatment section provided at a distal end side of the insertion section; and a detected means provided at the manipulation section and detected by the manipulation section position-orientation detecting means.

According to a twelfth aspect of the present invention, in the surgical instrument according to the eleventh aspect, the detected means may be markers.

According to a thirteenth aspect of the present invention, in the surgical instrument according to the eleventh or twelfth aspect, the detected means may further include an indicator section configured to enable the manipulation section position-orientation detecting means to identify geometric characteristics of the manipulation section.

DETAILED DESCRIPTION OF THE PREFERRED EMBODIMENTS (First Embodiment)

Figure 1:
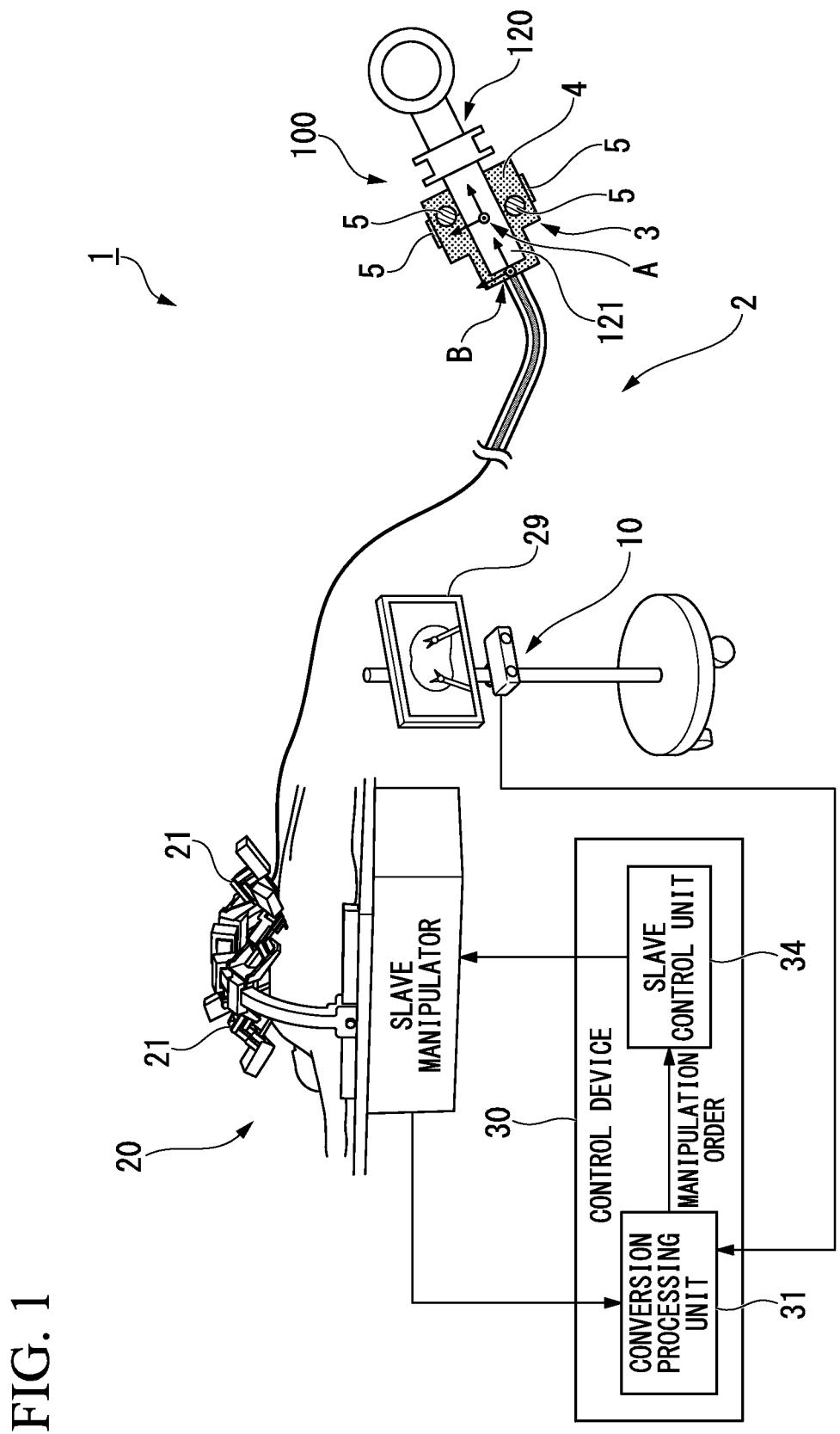
FIG. 1 is an overall view showing an operation support device according to a first embodiment of the present invention.
Figure 2:
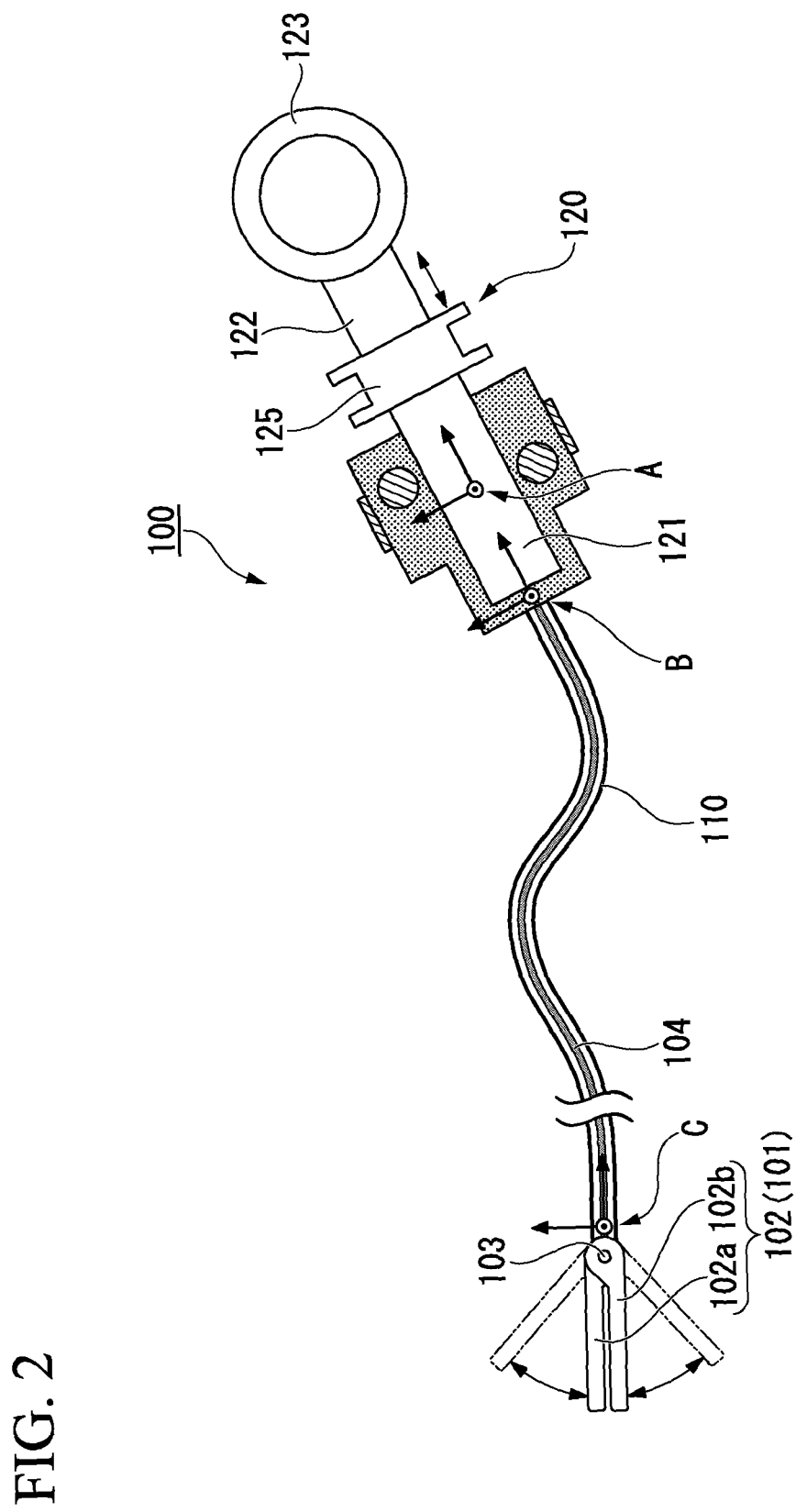
FIG. 2 is a schematic view of a surgical instrument used with the operation support device according to the first embodiment of the present invention.
Figure 3:
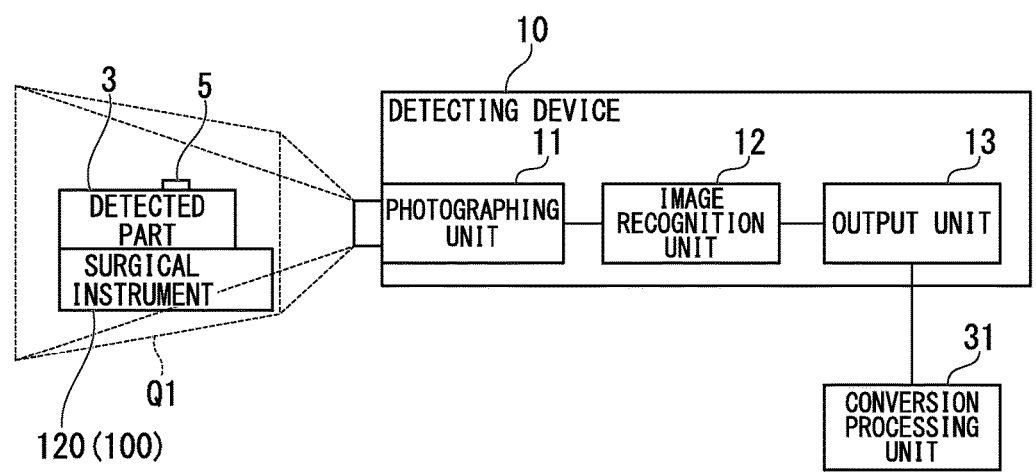
FIG. 3 is a block diagram of a detecting device in the operation support device according to the first embodiment of the present invention.
Figure 4:
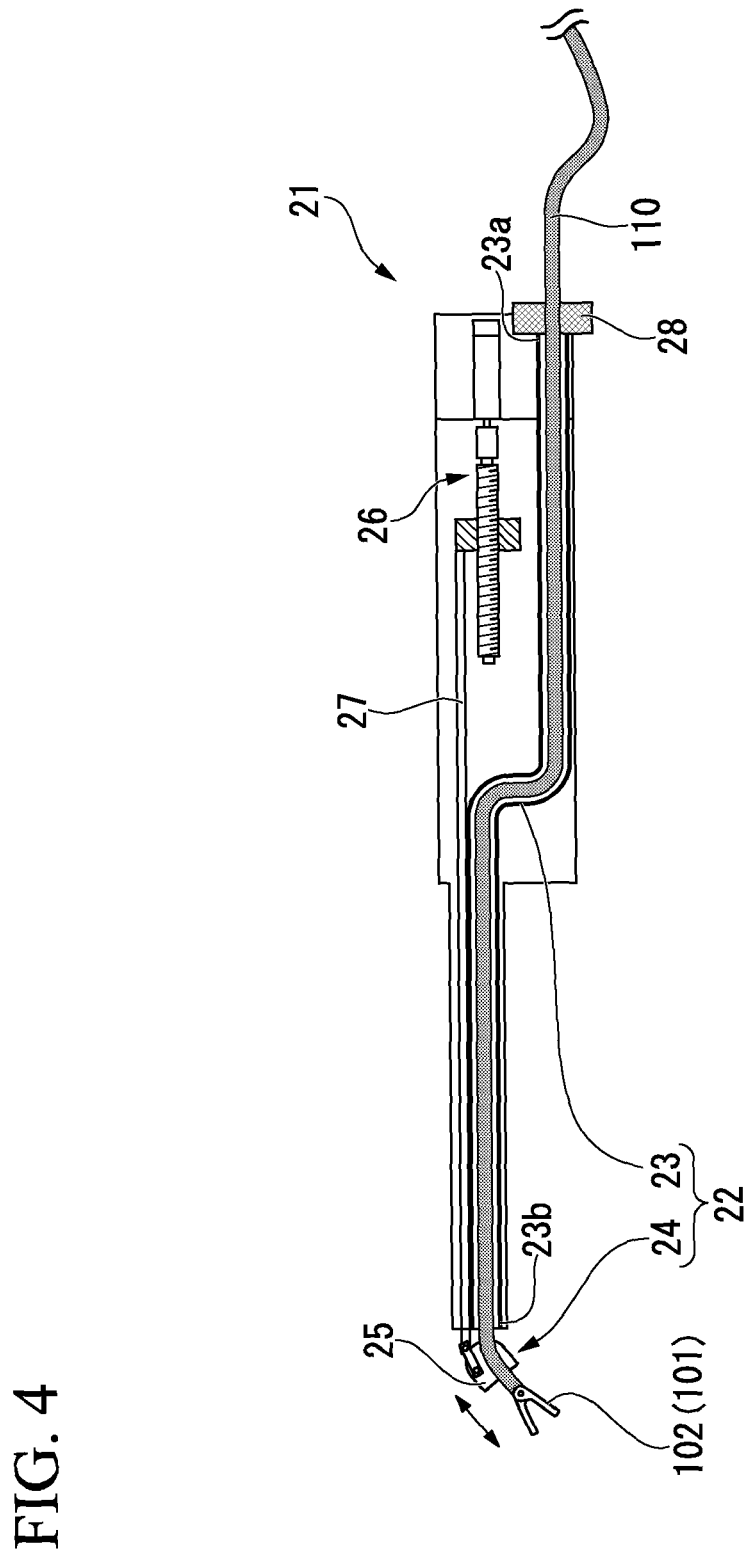
FIG. 4 is a schematic view showing a portion of a slave manipulator in the operation support device according to the first embodiment of the present invention.
Figure 5:
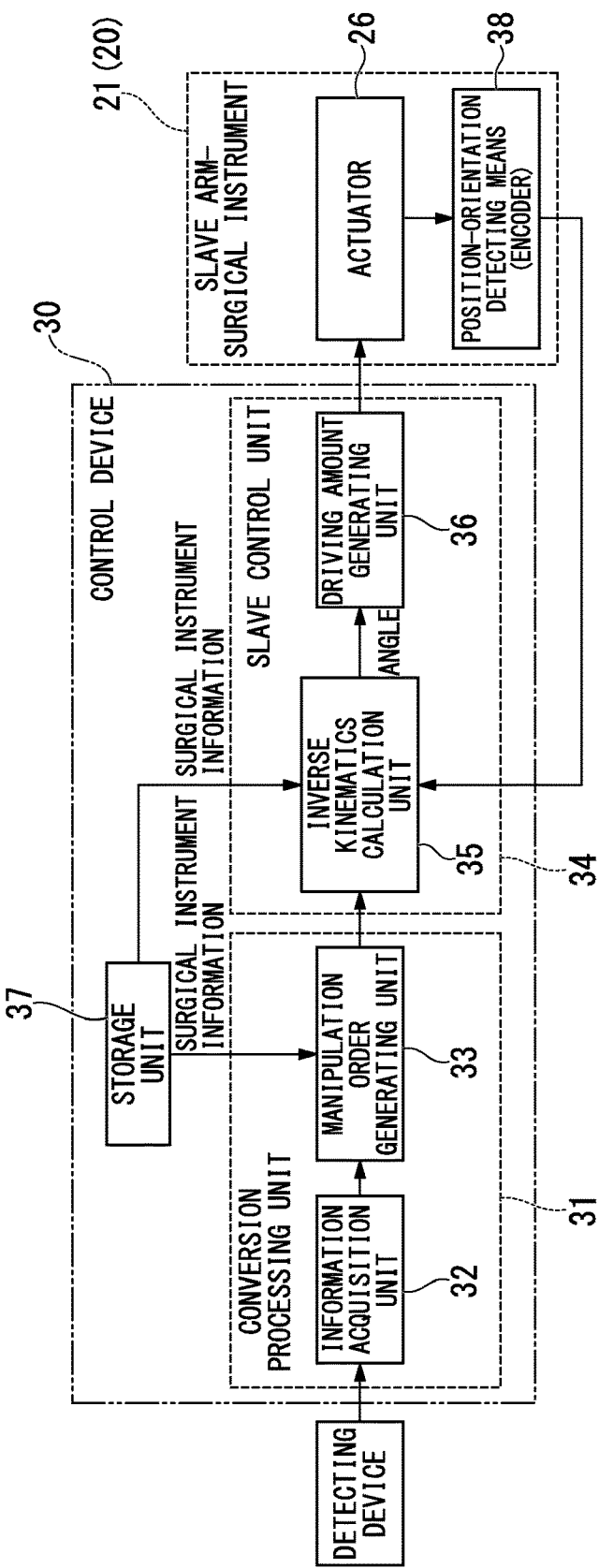
FIG. 5 is a block diagram of a control device and a slave arm in the operation support device according to the first embodiment of the present invention.

An operation support device according to a first embodiment of the present invention will be described. FIG. 1 is an overall view showing the operation support device. FIG. 2 is a schematic view of a surgical instrument used with the operation support device. FIG. 3 is a block diagram of a detecting device in the operation support device. FIG. 4 is a schematic view showing a portion of a slave manipulator in the operation support device. FIG. 5 is a block diagram of a control device and a slave arm in the operation support device.

As shown in FIG. 1, an operation support device 1 includes a master manipulator 2 (a manipulation input unit), a slave manipulator 20 (an operating section), a display device 29, and a control device 30. The operation support device 1 is configured to be capable of attaching a known flexible treatment tool as a surgical instrument 100.

While the configuration of the surgical instrument 100 is not particularly limited, for example, as shown in FIG. 2, the surgical instrument 100 used by being attached to the operation support device 1 includes a treatment section 101, an insertion section 110, and a manipulation section 120.

As the treatment section 101, a known configuration to perform treatment with respect to a biological tissue, for example, a forceps, a needle, a high frequency knife, or the like, can be appropriately selected and employed. In the embodiment, the treatment section 101 is operated by manipulation in the manipulation section 120. The operations of the treatment section 101 may include, for example, opening-closing of a forceps, protrusion and withdrawal of a needle from the insertion section 110, electrical application of high frequency current to a high frequency knife, and so on. Hereinafter, an example in which a forceps 102 that can be opened and closed is installed as the treatment section 101 will be described.

The forceps 102 has a pair of forceps pieces 102a and 102b pivotally connected to each other by a pin 103. Further, a wire 104 configured to pivot the forceps pieces 102a and 102b about a central axis of the pin 103 is connected to the forceps pieces 102a and 102b. The wire 104 is connected to the forceps 102 at one end thereof, inserted into the insertion section 110, and connected to the manipulation section 120 at the other end.

The insertion section 110 is a flexible cylindrical member. In the embodiment, while the configuration of the insertion section 110 is not particularly limited as long as the configuration is a cylindrical shape, for example, the insertion section 110 has a coil sheath on which a metal wire is wound in a coil shape, and a covering member configured to cover the coil sheath. The above-mentioned wire 104 connected to the forceps pieces 102a and 102b is inserted into the insertion section 110.

The manipulation section 120 is fixed to the insertion section 110. Specifically, the manipulation section 120 includes a rod-shaped manipulation main body 121 having a front end to which the insertion section 110 is fixed, and a slider 125 connected to the manipulation main body 121 and fixed to the wire 104.

The manipulation main body 121 has a rail section 122 configured to hold the slider 125 to freely advance and retreat. The manipulation main body 121 has a finger hooking section 123 to hook an operator's finger and is formed at an opposite end of an end thereof to which the insertion section 110 is fixed.

The slider 125 is a substantially columnar member in which a depression is formed at an outer circumferential surface so as to be capable of hooking an operator's finger. As the slider 125 advances and retreats with respect to the manipulation main body 121, the wire 104 advances and retreats in the insertion section 110.

The surgical instrument 100 is configured such that at least the treatment section 101 can be sterilized. In addition, the surgical instrument 100 may be configured to be entirely sterilized.

The master manipulator 2 shown in FIG. 1 is installed to operate the slave manipulator 20 according to an operation by an operator. The master manipulator 2 includes a detected part 3 attached to the surgical instrument 100, and a detecting device 10 (a manipulation section position-orientation detecting means) configured to detect the detected part 3. In addition, the operation support device 1 has a manipulation input unit configured to issue a manipulation order for operating the slave manipulator 20. In the embodiment, the manipulation input unit is constituted by the master manipulator 2 and a conversion processing unit 31 in the control device 30.

The detected part 3 is attached to a position where is capable of avoiding an interference with gripping of the manipulation section 120 of the surgical instrument 100 by the operator. For example, in the embodiment, the detected part 3 is detachably fixed to the vicinity of a connecting portion between the manipulation main body 121 and the insertion section 110. The detected part 3 has a main body section 4 attached to the manipulation section 120, and a marker 5 installed in the main body section 4. In addition, the detected part 3 is configured to be entirely sterilizable. The detected part 3 is formed of a material appropriately selected to be sterilized by any one method of, for example, high pressure steam sterilization, ethylene oxide gas sterilization, sterilization by a liquid medicine such as alcohol, formalin, or the like, ultraviolet ray sterilization, and so on, or other sterilization methods.

A shape of the detected part 3 is not particularly limited. For example, the detected part 3 may be formed in a rectangular parallelepiped shape, a spherical shape, or the like. As the detected part 3 is configured to be sterilizable, a doctor or the like in a cleaned state can touch the detected part 3. Accordingly, the doctor or the like in the cleaned state can manipulate the detected part 3, and the doctor or the like who manipulates the detected part 3 can work in a cleaned field as he or she is. As a result, treatment such as surgery or the like can be more securely and efficiently performed.

The main body section 4 is a member having an outer surface at which the marker 5 is installed. The markers 5 installed in the main body section 4 are disposed at three places on an outer surface of the main body section 4 and spaced apart from each other. Each of the markers 5 has a predetermined color and shape. For example, in the embodiment, the plurality of markers 5 having the same shape, the same size and the same color are installed in the main body section 4. Each of the markers 5 is formed on the outer surface of the main body section 4 by, for example, printing.

The marker 5 is disposed by determining the position with respect to the main body section 4. For this reason, a position and an orientation of the marker 5 correspond to a position and an orientation of the main body section 4. Since the main body section 4 is fixed to the manipulation main body 121 of the manipulation section 120, the position and the orientation of the marker 5 correspond to the position and the orientation of the manipulation section 120.

When the three markers 5 are installed in the main body section 4, the three markers 5 are disposed at vertices of a triangle having three sides of different lengths. Accordingly, the orientation of the main body section 4 can be uniquely specified by a relative positional relation of each of the markers 5. Each of the markers 5 is installed on a planar portion or a curved portion in the outer surface of the main body section 4.

The marker 5 may be additionally installed in the main body section 4 to correspond to the case in which a certain marker 5 is shielded with respect to the detecting device 10 by an obstacle or the like during manipulation. When a certain marker 5 is shielded, the position and the orientation are obtained alternatively using the additionally installed marker 5.

Further, the three or more markers 5 may be disposed on one sheet and the sheet may be attached to the outer surface of the main body section 4.

As shown in FIG. 3, the detecting device 10 includes a photographing unit 11, an image recognition unit 12 and an output unit 13.

The photographing unit 11 is an apparatus configured to photograph the detected part 3 when the surgical instrument 100 to which the detected part 3 is attached is used by the operator. A photographing field of vision of the photographing unit 11 is set to photograph an entire space (hereinafter referred to as "a working space Q1") in which the detected part 3 is moved by the operator upon use of the operation support device 1. The photographing unit 11 includes at least a first camera configured to photograph the working space Q1 from one predetermined direction, and a second camera configured to photograph the working space Q1 from a direction different from the predetermined one direction. Accordingly, the photographing unit 11 can simultaneously photograph at least two images having different angles with respect to the detected part 3 positioned in the working space Q1. The photographing unit 11 may have three or more cameras. In addition, the photographing unit 11 may have a redundant configuration including a spare camera based on an assumption that an operator themself or another obstacle is interposed between the detected part 3 and the camera. The photographing unit 11 outputs the photographed image to the image recognition unit 12.

The image recognition unit 12 recognizes the marker 5 from the photographed image through image recognition processing. The image recognition unit 12 calculates a coordinate information as the position and the orientation of the marker 5 from the positional relation of each of the markers 5 in the working space Q1, and outputs the coordinate information to the output unit 13. The coordinate information calculated in the image recognition unit 12 is coordinate information (hereinafter referred to as "first coordinate information A," see FIG. 2) using a coordinate system intrinsic to the detected part 3.

The output unit 13 outputs the first coordinate information A calculated in the image recognition unit 12 to the conversion processing unit 31 of the control device 30. In the embodiment, the first coordinate information A output from the output unit 13 is information for specifying the position and the orientation of the detected part 3 by the conversion processing unit 31. The first coordinate information A is output from the output unit 13 according to a predetermined transmission timing regardless of whether or not the detected part 3 is moved in the working space Q1.

As shown in FIGS. 1 and 4, the slave manipulator 20 includes a slave arm 21 to which the endoscope apparatus and the surgical instrument 100 (which may be generally referred to hereinafter as "the surgical instrument 100 or the like"), and actuators (not shown) configured to operate the surgical instrument 100 or the like and the slave arm 21. Each of the actuators installed in the slave manipulator 20 is operated according to a driving signal output from the control device 30.

The endoscope apparatus installed in the slave manipulator 20 acquires an image of the treatment target or the surgical instrument 100 to output the image to the display device 29.

The slave arm 21 has an attachment section 22 configured to attach the surgical instrument 100. The attachment section 22 has a hollow section 23 into which the insertion section 110 is inserted, and a treatment section moving mechanism 24 configured to change a direction of the treatment section 101.

The hollow section 23 is opened to a proximal end section and a distal end section of the slave arm 21. A fixing section 28 to fix the insertion section 110 is installed in an opening 23a of the hollow section 23 disposed at the proximal end section of the slave arm 21. The treatment section 101 of the surgical instrument 100 is configured to protrude from or withdraw into an opening 23b formed in the distal end section of the slave arm 21.

The treatment section moving mechanism 24 has a holding section 25 to hold the distal end section of the insertion section 110 of the surgical instrument 100, and an actuator 26 for operating to bend the holding section 25.

The holding section 25 is installed in a distal end of the slave arm 21. In addition, for example, the holding section 25 has a clip or the like engaged with the outer surface of the insertion section 110. As the clip or the like is installed, useless rotation of the treatment section 101 about the central axis of the insertion section 110 can be prevented. Further, instead of the clip or the like engaged with the outer surface of the insertion section 110, a wall section, a cylindrical section, or the like, configured to support the outer surface of the insertion section 110 may be formed at the holding section 25. In this case, advance and retreat or rotation of the treatment section 101 with respect to the holding section 25 can be performed as needed.

While any portion of the insertion section 110 may be held by the holding section 25, in the embodiment, the outer surface of the insertion section 110 is attached to the holding section 25 at a slightly proximal side with respect to the treatment section 101. In the embodiment, the holding section 25 is configured to be bent at a slightly proximal side with respect to the treatment section 101 in a state that the surgical instrument 100 is attached to the holding section 25. The holding section 25 may be configured such that the insertion section 110 is attached by a worker through manual work. The holding section 25 may be configured such that the insertion section 110 is attached through remote manipulation with the clip moving by another power source (not shown). Hereinafter, an example having a configuration in which the insertion section 110 is attached or detached by operating the clip through the remote manipulation will be described.

In the embodiment, the actuator 26 is disposed in the slave arm 21 and connected to the holding section 25 via a connecting rod 27.

A position-orientation detecting means 38 (see FIG. 5) to detect the position and the orientation of the slave arm 21 and the position and the orientation of the treatment section moving mechanism 24 is installed in the slave arm 21. For example, the position-orientation detecting means 38 is an encoder or the like installed in the slave arm 21 itself or each joint shaft of the treatment section moving mechanism 24. The position and the orientation of the slave arm 21 and the position and the orientation of the treatment section 101 held by the holding section 25 can be calculated by solving kinematics from these joint displacement quantities.

As shown in FIG. 1, the display device 29 is attached to the same base as the detecting device 10 of the master manipulator 2, and disposed in front of the operator. The display device 29 has a display panel configured to display the image acquired by the endoscope apparatus. As the display panel, a liquid crystal panel, an organic EL panel, or the like can be appropriately selected and employed. In addition, the display panel may be a panel configured to display the image that is three-dimensionally visible. The panel configured to display the three-dimensionally visible image may employ a configuration in which images for a right eye and a left eye can be divided by special glasses, a configuration in which the image is three-dimensionally visible with the naked eye, or the like.

As shown in FIGS. 1 and 5, the control device 30 includes the conversion processing unit 31, a slave control unit 34 and a storage unit 37. The conversion processing unit 31 is connected to the detecting device 10. The slave control unit 34 is connected to the conversion processing unit 31, and connected to each of the actuators 26 of the slave manipulator 20. The storage unit 37 is connected to the conversion processing unit 31 and the slave control unit 34.

The conversion processing unit 31 includes information acquisition unit 32, and a manipulation order generating unit 33 connected to the information acquisition unit 32. The information acquisition unit 32 receives the first coordinate information A output from the detecting device 10 shown in FIG. 3.

The information acquisition unit 32 acquires the first coordinate information A calculated using the coordinate system intrinsic to the detected part 3 (see FIG. 1), and outputs the first coordinate information A to the manipulation order generating unit 33.

The first coordinate information A of the detected part 3 output from the detecting device 10 shown in FIG. 3 is input into the manipulation order generating unit 33 via the information acquisition unit 32. The first coordinate information A of the detected part 3 is input into the manipulation order generating unit 33 according to the predetermined transmission timing as tracking information of the detected part 3.

The manipulation order generating unit 33 has a coordinate system conversion function which converts a coordinate system of the tracking information of the detected part 3 into a coordinate system of the manipulation section 120 to which the detected part 3 is attached. The coordinate system of the manipulation section 120 is a coordinate system determined according to the position of the marker 5 in the detected part 3 and the shape of the manipulation section 120. In the embodiment, the coordinate system of the manipulation section 120 is a 3-dimensional coordinate system using a connecting position between the manipulation main body 121 and the insertion section 110 as an origin. The information which specifies the coordinate system of the manipulation section 120 is stored in the storage unit 37 as surgical instrument information, and the information is appropriately referred to by the manipulation order generating unit 33. Accordingly, the first coordinate information A in the tracking information of the detected part 3 is converted into coordinate information (hereinafter referred to as "second coordinate information B," see FIG. 2) according to a 3-dimensional coordinate system using the connecting position between the manipulation main body 121 and the insertion section 110 as the origin.

For example, the conversion of the coordinate system can be performed using a conversion matrix as expressed by the following Math 1.

[Equation. 1]

$$\{P_s\} = \{T\}\{P_m\} \quad \text{(Equation 1)}$$

In the above-mentioned Equation 1, $\{Pm\}$ is coordinates of the detected part 3 based on the coordinate system intrinsic to the detected part 3, $\{T\}$ is a known conversion matrix based on the surgical instrument information, and $\{Ps\}$ is coordinates of the manipulation section 120 using the connecting position between the manipulation main body 121 and the insertion section 110 as the origin.

The manipulation order generating unit 33 outputs a manipulation order for operating the slave manipulator 20 and the surgical instrument 100 shown in FIG. 1 to the slave control unit 34. The manipulation order issued by the manipulation order generating unit 33 includes, for example, the second coordinate information B showing the position and the orientation after movement of the slave arm 21 and the surgical instrument 100 serving as the manipulation target.

The slave control unit 34 includes an inverse kinematics calculation unit 35 connected to the conversion processing unit 31, and a driving amount generating unit 36 connected to the inverse kinematics calculation unit 35.

The inverse kinematics calculation unit 35 acquires tracking information of the slave manipulator 20 from the position-orientation detecting means 38 installed in the slave manipulator 20. The tracking information of the slave manipulator 20 is coordinate information (hereinafter referred to as "third coordinate information C") showing the position and the orientation of the treatment section 101 installed in the surgical instrument 100 with the positions and the orientations of the surgical instrument 100 and the slave arm 21. In the embodiment, the coordinate system in the tracking information of the slave manipulator 20 is a 3-dimensional coordinate system using a position of a slightly distal side with respect to the holding section 25 as the origin. In addition, in a state in which the surgical instrument 100 is attached to the holding section 25, a boundary portion between the treatment section 101 and the insertion section 110 becomes the origin of the coordinate system in the tracking information of the slave manipulator 20.

Further, in the embodiment, opening and closing angles of the forceps pieces 102a and 102b (see FIG. 2) in the treatment section 101 may not be included in the tracking information of the slave manipulator 20. This is because, since the forceps pieces 102a and 102b are directly connected to the slider 125 of the manipulation section 120 by the wire 104, manipulation feeling of the forceps pieces 102a and 102b is directly transmitted to the operator.

The inverse kinematics calculation unit 35 converts the manipulation order and output from the conversion processing unit 31 into moving angle information of each joint and the surgical instrument 100 in the slave manipulator 20 corresponding to the manipulation order from the manipulation order generating unit 33, and outputs the moving angle information to the driving amount generating unit 36.

The inverse kinematics calculation unit 35 may have a coordinate conversion function of matching the coordinate system of the second coordinate information B and the coordinate system of the third coordinate information C through coordinate conversion as needed. When the coordinate system of the second coordinate information B and the coordinate system of the third coordinate information C are matched by the coordinate conversion, the operator who moves the treatment section 101 while viewing the endoscope image can intuitively move the treatment section 101.

The inverse kinematics calculation unit 35 may have a scale conversion function of matching a scale in the tracking information of the detected part 3 and a scale in the tracking information of the slave manipulator 20.

An operation of the operator who moves the detected part 3 while viewing the display device 29 can be reflected in the operations of the slave manipulator 20 and the surgical instrument 100 by the coordinate conversion function and the scale conversion function.

The driving amount generating unit 36 outputs a driving signal defining a driving amount of each of the actuators 26 corresponding to the moving angle information output from the inverse kinematics calculation unit 35 to each of the actuators 26 of the slave manipulator 20.

Figure 6:
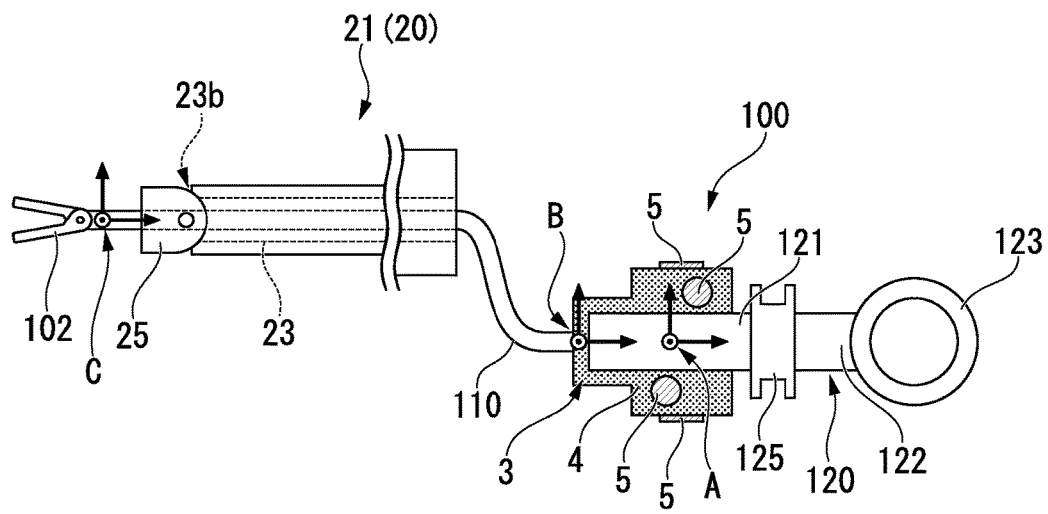
FIG. 6 is a schematic view showing a motion in use of the operation support device according to the first embodiment of the present invention.
Figure 7:
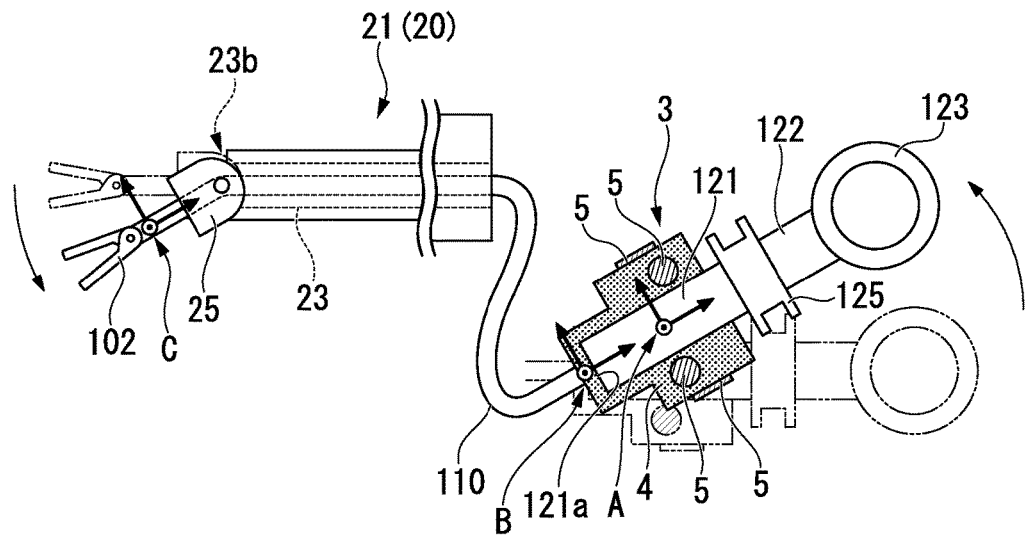
FIG. 7 is a schematic view showing a motion in use of the operation support device according to the first embodiment of the present invention.

Next, an operation and an action in use of the operation support device 1 of the embodiment will be described. FIGS. 6 and 7 are schematic views showing the operation in use of the operation support device.

In use of the operation support device 1, as shown in FIG. 6, the operator inserts the insertion section 110 of the surgical instrument 100 into the hollow section 23 of the slave arm 21. The outer surface of the insertion section 110 is attached to the holding section 25 at a position at which the treatment section 101 protrudes from the opening 23b of the hollow section 23 disposed at the distal end side of the slave arm 21. A work of attaching the insertion section 110 to the holding section 25 may also be performed through manual work by a clean person or may also be performed through remote manipulation. The surgical instrument 100 may be fixed using both of the clip of the holding section 25 and the fixing section 28 of the slave arm 21. The surgical instrument 100 may be fixed using any one of the clip of the holding section 25 and the fixing section 28 of the slave arm 21.

In use of the surgical instrument 100, the operator grips the manipulation section 120 of the surgical instrument 100, and as shown in FIG. 7, moves the manipulation section 120 as needed. Then, the detected part 3 attached to the manipulation section 120 is also integrally moved with the manipulation section 120, and the marker 5 installed in the detected part 3 is moved in the working space Q1. At this time, the marker 5 is photographed by the photographing unit 11 installed in the detecting device 10 shown in FIG. 3.

The detecting device 10 detects the position and the orientation of the marker 5 in the working space Q1, and outputs the first coordinate information A to the conversion processing unit 31 of the control device 30.

The first coordinate information A is coordinate-converted based on the first coordinate information A (the tracking information of the detected part 3) to generate the second coordinate information B by the manipulation order generating unit 33. In the conversion processing unit 31, the manipulation order (see FIG. 1) including the second coordinate information B is generated. The manipulation order generated by the manipulation order generating unit 33 is output to the inverse kinematics calculation unit 35 of the slave control unit 34.

In the inverse kinematics calculation unit 35, the second coordinate information B included in the manipulation order is compared with the tracking information (the third coordinate information C) of the slave manipulator 20 acquired from the slave manipulator 20. By using the compared result, the inverse kinematics calculation unit 35 calculates a moving angle of each joint configured to control the position and the orientation of the slave arm 21 and a moving angle of each joint configured to control the position and the orientation of the treatment section 101, and outputs the moving angles to the driving amount generating unit 36 as moving angle information.

In the driving amount generating unit 36, according to the moving angle information output from the inverse kinematics calculation unit 35, a driving signal for defining a driving amount of each of the actuators 26 of moving the slave arm 21 and the surgical instrument 100 is generated, and the slave arm 21 and the surgical instrument 100 are moved.

In the embodiment, an operation of varying a direction of a portion protruding from the distal end of the slave arm 21 in the surgical instrument 100 is performed by bending the holding section 25. As the slave arm 21 itself is moved, the position of the holding section 25 is moved, and thus the position and the orientation of the surgical instrument 100 can also be varied.

For example, as shown in FIG. 7, when the manipulation such as rotation of the manipulation section 120 with a distal end 121a of the manipulation main body 121 in the manipulation section 120 serving as a rotational center is performed by an operator, only the holding section 25 may be bent without movement of the slave arm 21 itself.

In the embodiment, the position and the orientation of the treatment section 101 are controlled based on the second coordinate information B. As a result, the operator can obtain a manipulation feeling as if the treatment section 101 were fixed to the connecting position between the manipulation main body 121 and the insertion section 110. That is, in the embodiment, the operator who manipulates the manipulation section 120 can use the surgical instrument 100 with a manipulation feeling as if he or she were using a hard instrument in which the forceps pieces 102a and 102b are attached to the distal end of the manipulation main body 121.

Next, opening-closing control of the forceps pieces 102a and 102b will be described.

As shown in FIG. 2, the forceps pieces 102a and 102b are connected to the wire 104. The wire 104 to which the forceps pieces 102a and 102b are connected extends to the manipulation section 120 through the insertion section 110. Further, in the manipulation section 120, the wire 104 is connected to the slider 125. For this reason, as the slider 125 is slid with respect to the manipulation main body 121, the forceps pieces 102a and 102b are opened and closed. A feeling when a tissue or the like is gripped by the pair of forceps pieces 102a and 102b is transmitted to the slider 125 through the wire 104, and transmitted to the operator who manipulates the slider 125 as the manipulation feeling.

Next, the case in which the surgical instrument 100 is attached or detached and used will be described.

In use of the operation support device 1 shown in FIG. 1, the surgical instrument 100 may be removed from the slave arm 21. For example, in the case in which a biopsy forceps is used as the surgical instrument 100, when the biopsy sample is removed to the outside of the body, only the surgical instrument 100 can be pulled to the outside of the body without removing the slave arm 21 from a patient, improving workability.

In this case, the clip of the holding section 25 (see FIG. 4) is moved by the remote manipulation to release the fixing state between the holding section 25 and the insertion section 110, and further, the fixing between the fixing section 28 of the slave arm 21 and the insertion section 110 of the surgical instrument 100 is released by, for example, manual work.

When any one of the clip of the holding section 25 and the fixing section 28 of the slave arm 21 is fixed, the fixing of the one may be released.

Since the insertion section 110 of the surgical instrument 100 is flexible, an insertion field is extracted from the hollow section 23 by pulling the insertion section 110 from the hollow section 23 of the slave arm 21 even in a state in which the slave arm 21 and the holding section 25 are bent. The insertion section 110 can also be inserted into the hollow section 23 again as needed. In this case, the treatment section 101 disposed at the distal end of the insertion section 110 is guided to the same position as before extraction of the surgical instrument 100. After that, the clip of the holding section 25 is moved by the remote manipulation to fix the insertion section 110 to the holding section 25, enabling continuation of the work.

As described above, according to the operation support device 1 of the embodiment, the detected part 3 is installed in the manipulation section 120 of the surgical instrument 100, and the position and the orientation of the detected part 3 are specified by the detecting device 10, and the position and the orientation of the surgical instrument 100 are controlled. For this reason, control of the position and the orientation of the slave manipulator 20, control of the position and the orientation of the surgical instrument 100, and further manipulation of the treatment section 101 installed in the surgical instrument 100 can be easily performed by the operator alone.

In addition, since the position and the orientation of the detected part 3 are detected by the marker 5 that does not vary from a disposition relation previously determined in the main body section 4, remote manipulation and input can be precisely performed with a simple configuration.

In addition, in the embodiment, the flexible insertion section 110 is fixed to the fixing section 28 of the slave arm 21. When the manipulation section 120 is moved in the working space Q1, the treatment section 101 is moved as the slave arm 21 and the holding section 25 are moved without a force directly transmitted from the manipulation section 120 to advance and retreat or rotate the insertion section 110.

Accordingly, the position and the orientation of the treatment section 101 can be smoothly varied without occurrence of a problem in which the manipulation amount of the manipulation section 120 does not correspond to the movement amount of the treatment section 101 due to influence of a frictional resistance or the like between the hollow section 23 of the slave arm 21 and the insertion section 110 of the surgical instrument 100.

(Modified Example 1)

Next, a modified example of the embodiment will be described. FIGS. 8 to 12 are schematic views showing a configuration of the modified example.

In the modified example, the coordinate system in the detected part 3 is defined in advance such that the origin of the coordinate system intrinsic to the detected part 3 is converted into the origin of the coordinate system intrinsic to the manipulation section 120. In the case of the modified example, in the detected part 3, the manipulation section 120 having a specific shape corresponding to the detected part 3 is previously determined.

Figure 8:
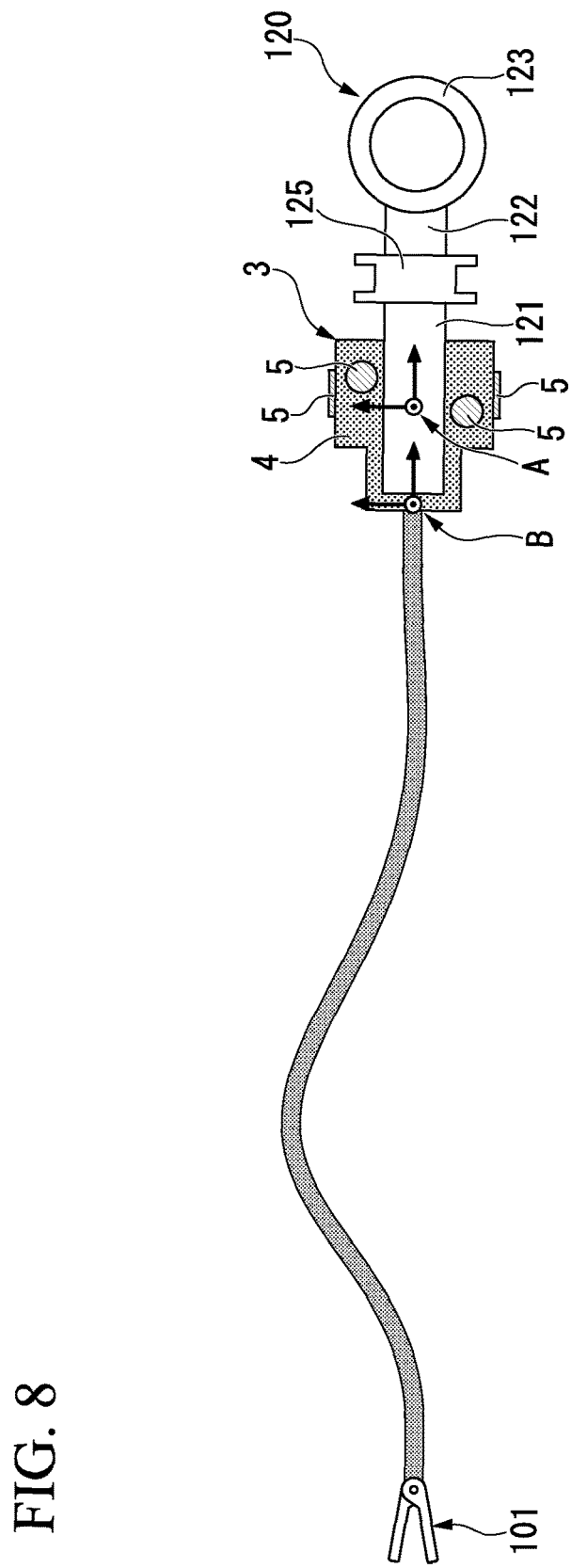
FIG. 8 is a schematic view showing a configuration of a modified example of the first embodiment of the present invention.
Figure 9:
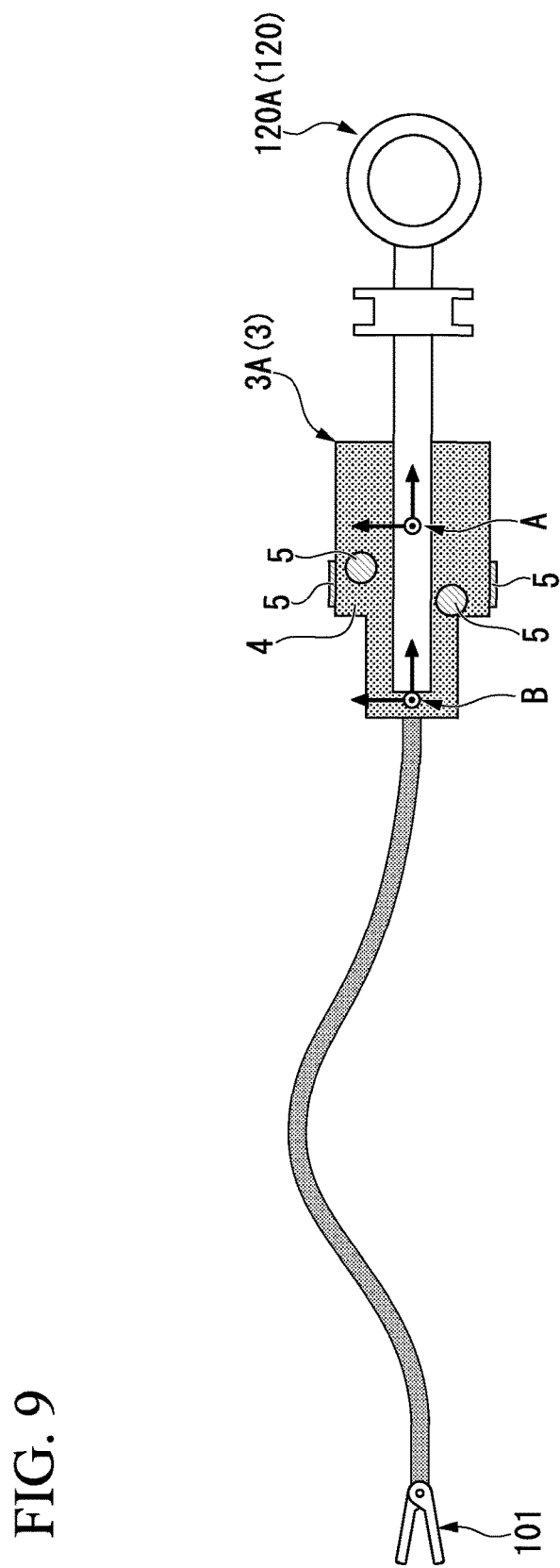
FIG. 9 is a schematic view showing the configuration of the modified example of the first embodiment of the present invention.

Specifically, for example, in a plurality of detected parts 3 and 3A having different shapes corresponding to the shape of the manipulation section 120, when the position of the marker 5 has a certain positional relation with respect to the connecting position between the manipulation main body 121 and the insertion section 110, the connecting position between the manipulation main body 121 and the insertion section 110 can be set to the origin of the second coordinate information B regardless of the shape of the detected part 3. For example, as shown in FIGS. 8 and 9, the detected part 3 corresponding to the manipulation section 120 is provided, and the detected part 3A corresponding to another manipulation section 120A is provided.

Figure 10:
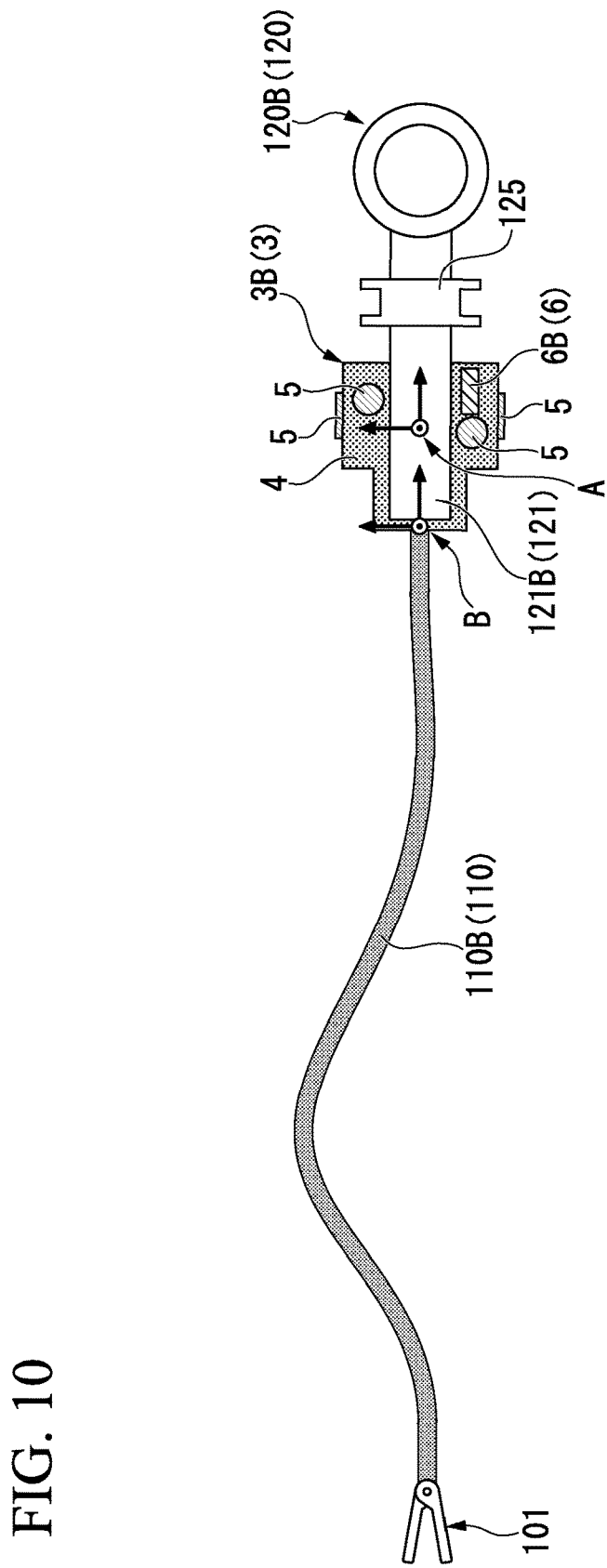
FIG. 10 is a schematic view showing the configuration of the modified example of the first embodiment of the present invention.
Figure 11:
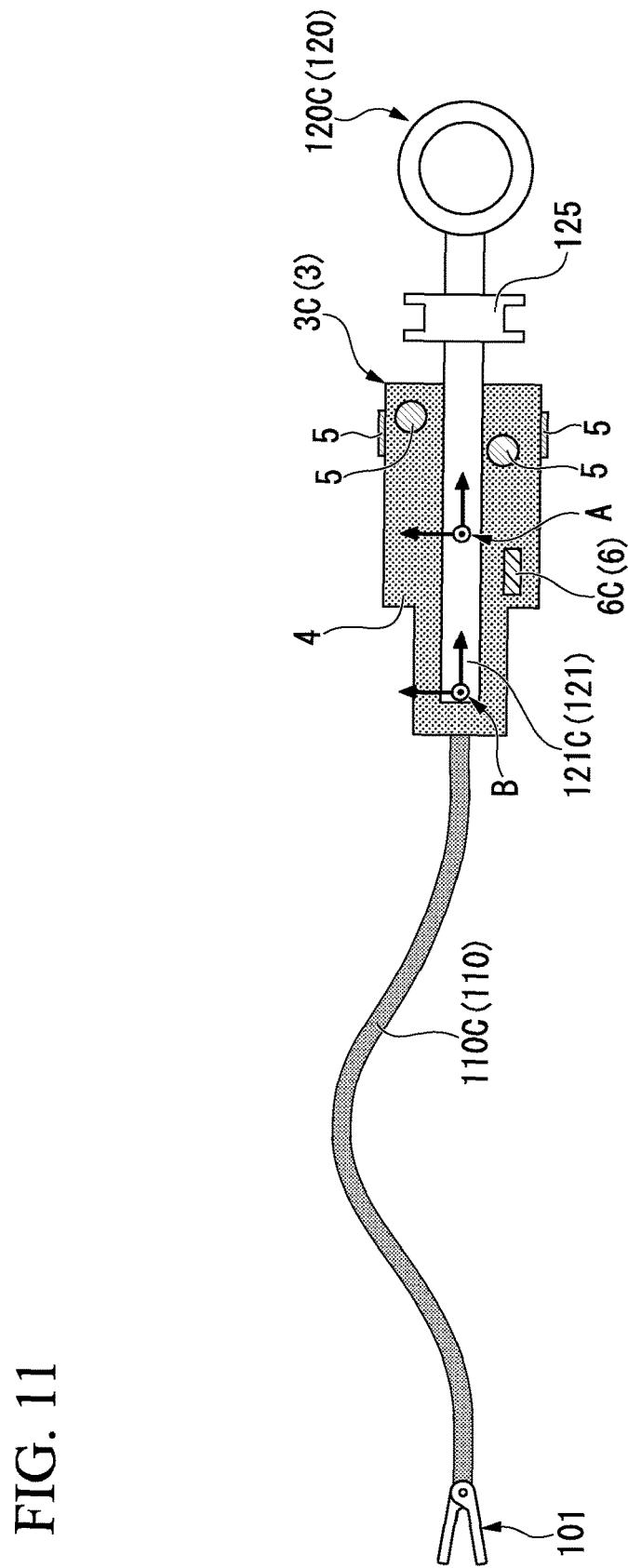
FIG. 11 is a schematic view showing the configuration of the modified example of the first embodiment of the present invention.
Figure 12:
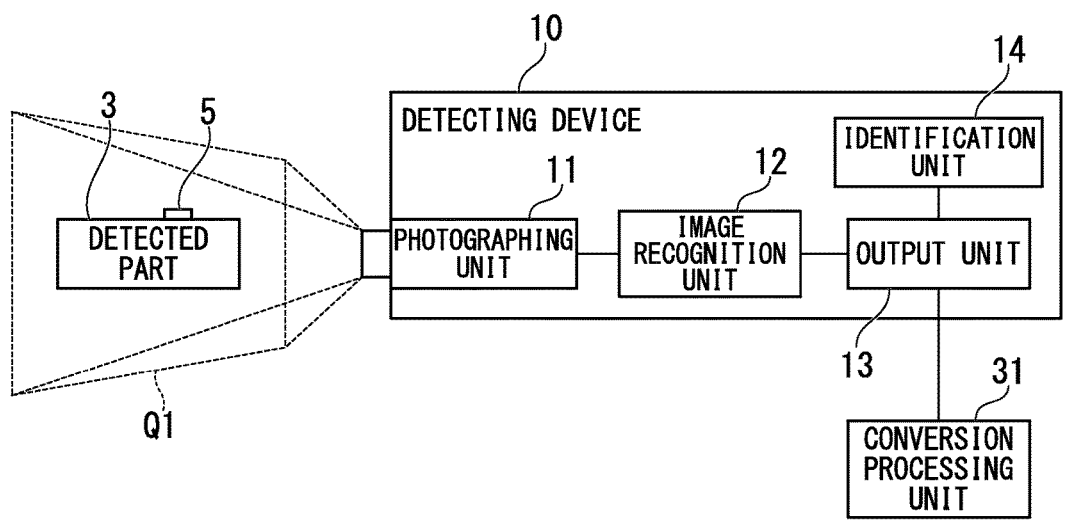
FIG. 12 is a schematic view showing the configuration of the modified example of the first embodiment of the present invention.

As another method, a means enabling the detecting device 10 to identify geometric characteristics of the manipulation section 120 may be provided at the detected part 3 or the manipulation section 120. For example, as shown in FIGS. 10 and 11, the indicator section 6 configured to enable the detecting device 10 to identify the manipulation section 120 having the corresponding specific shape is installed in the detected part 3. As shown in FIG. 12, an identification unit 14 configured to recognize the indicator section 6 and identify the surgical instrument 100 is installed in the detecting device 10.

Specifically, for example, as shown in FIG. 10, the detected part 3B corresponding to the manipulation section 120B is installed in the manipulation main body 121B. As shown in FIG. 11, the detected part 3C corresponding to the separate manipulation section 120C is installed in the manipulation main body 121C.

Surgical instrument information defined based on the shape of the manipulation section 120B or information which specifies the surgical instrument information are held in an indicator section 6B installed in the detected part 3B. Surgical instrument information defined based on the manipulation section 120C and information which specifies the surgical instrument information are held in an indicator section 6C installed in the detected part 3C.

The indicator sections 6B and 6C can appropriately select and employ, for example, the kind of the manipulation section 120 by, for example, combination of a pattern of a specific shape separately formed from the marker 5, a wireless tag separately installed from the marker 5, or disposition of the marker 5.

The identification unit 14 of the detecting device 10 stores information for defining the position of the origin of the second coordinate information B in the plurality of instruments 100 corresponding to the indicator section 6.

In the modified example, the indicator section 6 is recognized by the detecting device 10 while the marker 5 is detected by the detecting device 10. For example, when the pattern separately formed from the marker 5 is the indicator section 6, the indicator section 6 is photographed by the photographing unit 11 in the working space Q1, and the origin of the second coordinate information B corresponding to the pattern of the indicator section 6 is set. When the indicator section 6 is deviated from the photographing field of vision of the photographing unit 11 and another indicator section 6 is photographed by the photographing unit 11, the origin of the second coordinate information B is reset to correspond to another indicator section 6.

The operation support device of the modified example has the above-mentioned configuration, and thus can reduce calculation for converting the coordinate system during use of the certain manipulation section 120. In addition, when the surgical instrument 100 is exchanged with a new one during surgery or the like, since the setting of the origin appropriately corresponding to the manipulation section 120 of each of the treatment sections 101 is automatically performed, manipulation performance is improved.

In the modified example, the surgical instrument information in the storage unit 37 may be set based on the information held in the indicator section 6.

In the modified example, the position of the origin of the second coordinate information B may be set to the position other than the connecting position between the manipulation main body 121 and the insertion section 110. In addition, based on the technology disclosed in the modified example, the origin may also be set to the position of the manipulation section 120 having no configuration corresponding to the manipulation main body 121 or the insertion section 110.

(Modified Example 2)

Figure 13:
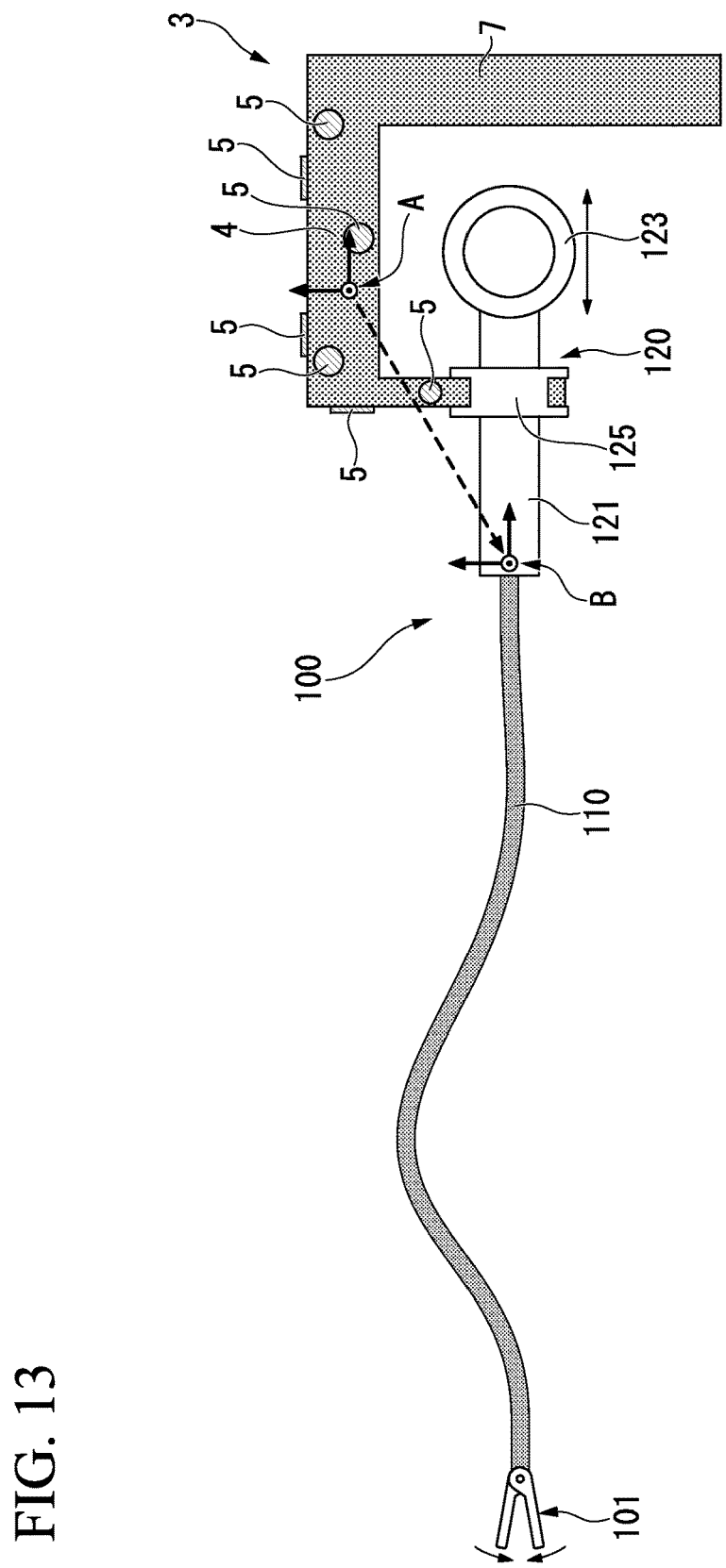
FIG. 13 is a schematic view showing another modified example of the first embodiment of the present invention.

Next, another modified example of the embodiment will be described. FIG. 13 is a schematic view showing the modified example.

As shown in FIG. 13, in the modified example, the detected part 3 has a gripping section 7 attached to the slider 125 of the manipulation section 120 and gripped by the operator. The marker 5 is installed in the detected part 3 as in the first embodiment.

In the modified example, the operator grips the gripping section 7 of the detected part 3, and hooks his/her finger on the finger hooking section 123 of the manipulation main body 121 to perform manipulation of the manipulation section 120.

In the modified example, the second coordinate information B described in the first embodiment is, for example, a coordinate information which is based on the 3-dimensional coordinate system with an origin at the connecting position between the manipulation main body 121 and the insertion section 110 at where the manipulation main body 121 is fully pulled toward the gripping section 7 with respect to the slider 125. For this reason, in the modified example, the manipulation main body 121 advances and retreats with respect to the origin in the second coordinate information B.

Even in the above-mentioned configuration, the same effect as the above-mentioned first embodiment is exhibited.

In the modified example, the operator performs the manipulation of the treatment section 101 by gripping the gripping section 7 of the detected part 3 and by hooking his/her finger on the manipulation main body 121 to move the manipulation main body 121. In this case, in the working space Q1, relative movement such as advance and retreat of the manipulation main body 121 with respect to the gripping section 7 occurs without movement of the gripping section 7. In the modified example, the origin in the second coordinate information B is an origin which is fixed a position relation with respect to the gripping section 7. For this reason, the origin in the second coordinate information B is related to the hand that grips the gripping section 7, and the operator can intuitively perform the manipulation.

In addition, in the modified example, like the above-mentioned first embodiment, a detection section attached to the manipulation main body 121 may be further installed.

(Second Embodiment)

Figure 14:
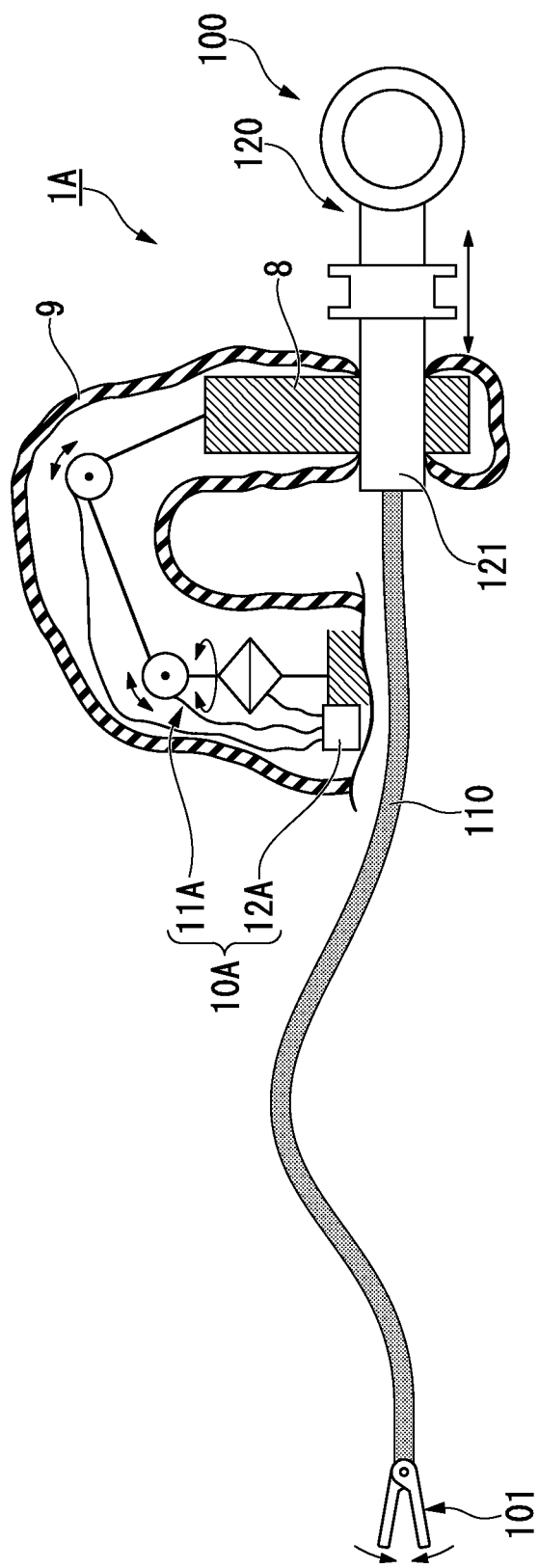
FIG. 14 is a schematic view showing a portion of an operation support device of a second embodiment of the present invention.
Figure 15:
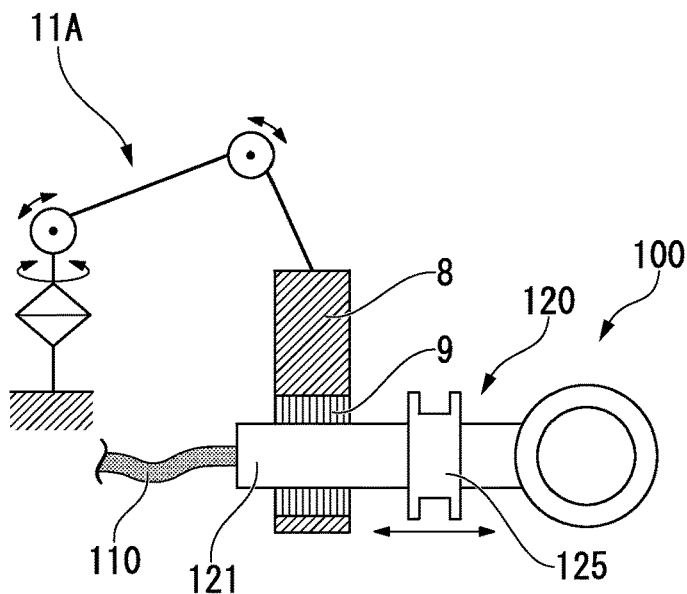
FIG. 15 is a schematic view showing another configuration example of the second embodiment of the present invention.
Figure 16:
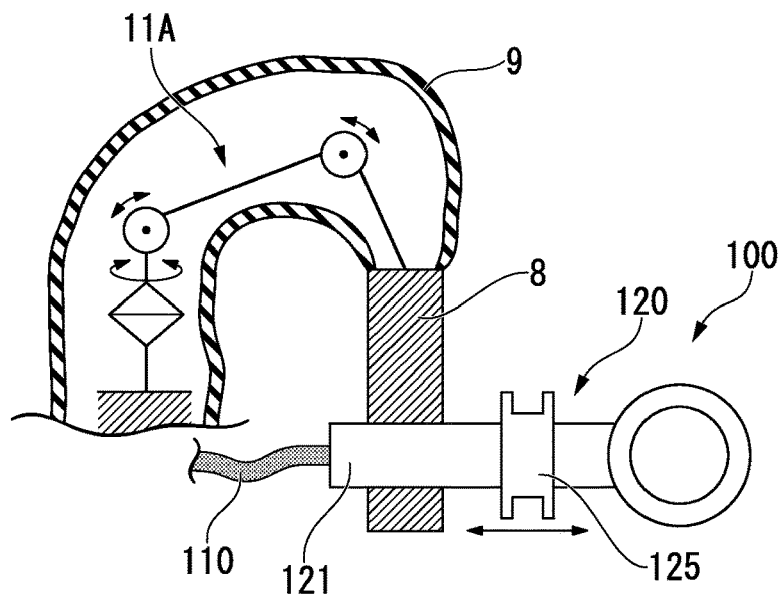
FIG. 16 is a schematic view showing still another configuration example of the second embodiment of the present invention.

Next, an operation support device according to a second embodiment of the present invention will be described. FIG. 14 is a schematic view showing a portion of the operation support device of the embodiment. FIG. 15 is a schematic view showing another configuration example of the embodiment. FIG. 16 is a schematic view showing still another configuration example of the embodiment.

As shown in FIG. 14, an operation support device 1A of the embodiment has an adapter 8 (a manipulation section position-orientation detecting means) attached to the manipulation section 120 instead of the detected part 3 having the marker 5 described in the above-mentioned first embodiment.

The adapter 8 and the manipulation section 120 are connected via an intermediate member 9 that can be sterilized. In the embodiment, the intermediate member 9 is a drape formed in a bag shape. Accordingly, the manipulation section 120 is maintained clean.

The operation support device 1A includes a detecting device 10A (a manipulation section position-orientation detecting means) including an articulated arm 11A connected to the adapter 8 and a position-orientation detecting unit 12A, instead of the detecting device 10 including the photographing unit 11 and the image recognition unit 12. The position-orientation detecting unit 12A detects a position and an orientation of the articulated arm 11A.

In the embodiment, the articulated arm 11A is covered in use using the drape as the above-mentioned intermediate member 9 interposed between the adapter 8 and the manipulation section 120.

The position-orientation detecting unit 12A includes an angle sensor such as an encoder or the like, which detects a moving angle of each joint of the articulated arm 11A, and acquires coordinates of the detected part 3 based on information of an angle output from the angle sensor.

The detecting device 10A has the same output unit 13 as in the first embodiment, and can output tracking information of the adaptor 8 to the conversion processing unit 31 through the output unit 13.

In the embodiment, the position and the orientation of the detection body 3 are specified by using the articulated arm 11A, instead of detection of the marker 5 in the working space Q1 of the first embodiment (see FIG. 3).

Even in the above-mentioned configuration, the same effect as in the above-mentioned first embodiment is exhibited. In addition, in the embodiment, since it is possible to prevent the marker 5 from being shielded by an obstacle and not being photographed by the photographing unit 11, the tracking information of the detected part 3 can be securely obtained.

As shown in FIG. 15, in the embodiment, the intermediate member 9 may not be the drape. For example, an annular member interposed between the adapter 8 and the manipulation section 120 may be employed as the intermediate member 9.

As shown in FIG. 16, in the embodiment, instead of covering the adapter 8 by using the drape as the intermediate member 9, the adapter 8 can be sterilized, and the sterilized drape (the intermediate member 9) may be fixed to the adapter 8.

Hereinabove, while the embodiments of the present invention have been described with reference to the accompanying drawings in detail, a specific configuration is not limited to the embodiments but may include design changes without departing from the spirit of the present invention.

For example, the treatment section moving mechanism 24 may have a function of rotating the treatment section 101 about an axis of the insertion section 110.

In addition, components shown in the above-mentioned embodiments and modified examples may be appropriately combined and configured.

Further, design changes with respect to the specific configuration are not limited to the above-mentioned matters.

What is claimed is:

1. An operation support device comprising:
   a surgical instrument comprising:
      an insertion section;
      a manipulation section provided at a proximal end side of the insertion section; and
      a treatment section provided at a distal end side of the insertion section;
   a slave arm configured to support at least the distal end side of the surgical instrument and to allow the treatment section to approach a treatment target;
   a camera system configured to detect information related with position or orientation of the manipulation section; and
   a controller comprising one or more processors, the one or more processors configured to:
      calculate a manipulation instruction based on the information from the camera system; and
      control a position or an orientation of the surgical instrument by controlling a movement of the slave arm based on the manipulation instruction.

2. The operation support device according to claim 1, wherein the controller is configured to use a coordinate system with an origin which is set to have a predetermined positional relation with respect to the manipulation section.

3. The operation support device according to claim 1, wherein the surgical instrument further comprises a marker provided at the manipulation section, and the camera system is configured to detect the information by detecting a position or an orientation of the marker.

4. The operation support device according to claim 2, wherein the surgical instrument further comprising an indicator section configured to enable the camera system to identify geometric characteristics of the manipulation section, and
   the camera system is configured to identify the indicator section so as to set the origin of the coordinate system.

5. The operation support device according to claim 1, wherein the slave arm further comprising a hollow section configured to receive both the insertion section and the treatment section, and the treatment section configured to protrude from an opening at a distal end of the hollow section.

6. The operation support device according to claim 1, wherein the slave arm further comprising a treatment section moving mechanism configured to move the treatment section by holding the distal end side of the insertion section and bending the distal end side of the insertion section.

7. The operation support device according to claim 1, wherein the surgical instrument further comprising a detected part detachably provided at the manipulation section for detecting the information by the camera system.

8. The operation support device according to claim 1, wherein the camera system comprising:
   an adapter configured to detachably attach to the manipulation section;
   an articulated arm configured to connect to the manipulation section via the adapter; and
   a sensor configured to detect a moving angle of each joint of the articulated arm.

9. The operation support device according to claim 7, wherein the detected part is sterilizable.

10. The operation support device according to claim 7, wherein the detected part is attached to the manipulation section via an intermediate member which is sterilized.

11. A surgical instrument for an operation support device which comprises a slave arm configured to support at least a distal end side of the surgical instrument, and a controller comprising one or more processors, the one or more processors configured to control a movement of the slave arm so as to assist an approach of the slave arm toward a distal end of the surgical instrument, the surgical instrument comprising:
   a manipulation section;
   an elongated section provided at a distal end side of the manipulation section;
   an end effector provided at the distal end side of the elongated section; and
   a marker disposed at the manipulation section;
   wherein the one or more processors are configured to:
      recognize a position or an orientation of the marker from an image of a camera of the operation support device;
      generate coordinate information from the position or the orientation of the marker;

calculate a manipulation instruction based on the coordinate information; and control the slave arm based on the manipulation instruction.

12. The surgical instrument according to claim 11, further comprising an indicator section configured to identify geometric characteristics of the manipulation section.

13. The surgical instrument according to claim 11, further comprising a detected part detachably attached to the manipulation section, wherein the marker is disposed at the detected part.

14. An operation support device comprising:
a surgical instrument comprising:
a manipulation section;
an elongated section provided at a distal end side of the manipulation section;
a end effector provided at a distal end side of the elongated section; and
a marker disposed at the manipulation section;
a slave arm which includes a hollow section configured to receive both the elongated section and the end effector;
a camera configured to photograph the marker; and
a controller comprising one or more processors, the one or more processors configured to:
recognize a position or an orientation of the marker from an image of the camera;
generate a coordinate information from the position or the orientation of the marker;
generate a manipulation instruction based on the coordinate information; and
control the slave arm based on the manipulation instruction.

15. The operation support device according to claim 14, wherein the coordinate information uses a coordinate system with an origin which is set to have a predetermined positional relation with respect to the manipulation section.

16. The operation support device according to claim 15, further comprising:
an indicator section disposed at the manipulation section;
wherein the indicator section is configured to identify geometric characteristics of the manipulation section so as to set the origin of the coordinate system.

17. An operation support device comprising:
a surgical instrument comprising:
a manipulation section ;
an elongated section provided at a distal end side of the manipulation section; and
a end effector provided at a distal end side of the elongated section;
a detected part;
a marker disposed at the detected part;
a slave arm which includes a hollow section configured to receive both the elongated section and the end effector;
a camera configured to photograph the marker; and
a controller comprising one or more processors, the one or more processors configured to:
recognize a position or an orientation of the marker from an image of the camera;
generate a coordinate information from the position or the orientation of the marker;
generate a manipulation instruction based on the coordinate information; and
control the slave arm based on the manipulation instruction.

18. The operation support device according to claim 17, wherein the coordinate information uses a coordinate system with an origin which is set to have a predetermined positional relation with respect to the manipulation section.

19. The operation support device according to claim 18, further comprising:
an indicator section disposed at the detected part;
wherein the indicator section is configured to identify geometric characteristics of the manipulation section, and to enable to set the origin of the coordinate system.

20. An operation support device comprising:
a surgical instrument comprising:
a manipulation section;
an elongated section provided at a distal end side of the manipulation section; and
an end effector provided at a distal end side of the elongated section;
a slave arm which includes a hollow section configured to receive both the elongated section and the end effector;
an adapter configured to connect to the manipulation section;
an articulated arm configured to connect to the manipulation section via the adapter;
a sensor configured to detect a moving angle of each joint of the articulated arm; and
a controller comprising one or more processors, the one or more processors configured to:
generate a coordinate information of the manipulation section from the moving angle detected the sensor;
calculate a manipulation instruction based on the coordinate information; and
control the slave arm based on the manipulation instruction.

21. The operation support device according to claim 20, wherein the adapter is sterilizable.

22. The operation support device according to claim 20, wherein the adapter is attached to the manipulation section via an intermediate member which is sterilized.

* * * * *